United States Patent [19]

Elliott

[11] 4,175,207

[45] Nov. 20, 1979

[54] VISUAL-TYPE HYGROMETER

[76] Inventor: Stanley B. Elliott, 7125 Cohelly Blvd., Bedford, Ohio 44146

[21] Appl. No.: 795,163

[22] Filed: May 9, 1977

Related U.S. Application Data

[60] Continuation of Ser. No. 547,811, Feb. 7, 1975, abandoned, which is a continuation-in-part of Ser. No. 505,526, Sep. 12, 1974, abandoned, which is a continuation-in-part of Ser. No. 245,494, Apr. 19, 1972, abandoned, which is a division of Ser. No. 18,921, Mar. 12, 1970, abandoned.

[51] Int. Cl.$^2$ ............................................. C07C 65/20
[52] U.S. Cl. .................................... 562/460; 562/488
[58] Field of Search ........................................ 562/460

[56] References Cited

U.S. PATENT DOCUMENTS

| 3,203,982 | 8/1965 | McCracken et al. ................. 260/515 |
|---|---|---|
| 3,510,513 | 5/1970 | McCracken et al. ................. 260/517 |
| 3,526,048 | 9/1970 | Rowland et al. ...................... 38/144 |
| 3,776,038 | 12/1973 | Elliot ..................................... 73/335 |

*Primary Examiner*—Jane S. Myers
*Attorney, Agent, or Firm*—Baldwin, Egan, Walling & Fetzer

[57] ABSTRACT

A composition of matter for use in a visual-type instrument which includes a polarizer for a light beam and an analyzer for a light beam, the chemical composition being birefringent at a first relative humidity and non-birefringent at a second relative humidity.

7 Claims, 6 Drawing Figures

VISUAL-TYPE HYGROMETER

This application is a continuation of my copending application Ser. No. 547,811, filed Feb. 7, 1975, entitled "Visual Type Hygrometer," which in turn is a continuation-in-part of my application Ser. No. 505,526, filed Sept. 12, 1974, entitled "Visual-Type Hygrometer" which, in turn, is a continuation-in-part of my application Ser. No. 245,494, filed Apr. 19, 1972 entitled "Visual-Type Hygrometer" and which is a division of my application Ser. No. 18,921, filed March 12, 1970, entitled "Visual-Type Hygrometer," which prior applications are now abandoned.

This invention relates to a type of hygrometer in which changes of relative humidity (R.H.) are indicated visually. More specifically, birefringent crystals whose birefringence is sensitive to changes in relative humidity are displayed between a polarizer and analyzer so that changes in birefringence may be readily observed. As is well known in the art, with the exception of crystals of the cubic system, or as also referred to in the art as "non-cubic systems," all fragments of crystals act on polarized light. By selection of suitable birefringent crystallizable compounds, whose birefringence either begins or terminates at various relative humidities, a series of highly visual displays may be readily assembled to comprise an efficient hygrometer.

Compounds may be selected whose crystalline, birefringent, hydrated form is either reversible or irreversible. As I describe in more detail later, an hygrometer may be desired which is similar to an ordinary household hygrometer: Its indicating function is essentially permanently reversible. Or a "recording" hygrometer may be desired in which a visual plaque does not revert to its nonbirefringent form even though the ambient humidity subsequently drops below the R.H. which originally triggered it.

The reversible compounds are those whose structure is (a) not sensitive to polymorphic or polytypic changes and which are carefully kept free of nuclei which might hasten such changes, or (b) inherently resistant to any polymorphic or polytypic changes. The irreversible compounds, in contrast, are those whose structure is (a) somewhat sensitive to polymorphic or polytypic changes and in which nucleating agents (such as crystals of the "condensed phase") are deliberately included, or (b) very susceptical to rapid, spontaneous polymorphic or polytypic changes. Each of these two classes—reversible and irreversible—have important industrial uses in signalling or recording changes in humidity (or temperature).

In the prior art U.S. Pat. No. 3,510,513 of Gulf Research and Development Co., composition solutions of alkali metal salts of 3,3',4,4' benzophenone tetracarboxylate are taught for use in chemical processing for the separation of solid catalysts. In this patented concept it is only the acid which is in solid slurry form. At no time in the process of said patent is a solid alkali salt of a benzophenone carboxylic acid prepared or mentioned. Rather, since the catalyst is a solid, the alkali salt must be a filterable solution.

In contract, this application is exclusively concerned with the solid forms of alkali metal 3,3',4,4' benzophenone tetracarboxylates or complexes of these carboxylates, for it is the crystalline, hydrated, birefringent form of these compounds which perform the unique signalling functions described in these specifications when certain relative humidities are reached.

BACKGROUND

There are many accurate hygrometers available whose operation depends on such factors as (1) the change in length of a hair or membrane as the R.H. varies, (2) the ability of a hygroscopic solution film to change its electrical resistance with changes in moisture content (R.H.) of the gas above it, (3) the ability of a hygroscopic polymeric sensor to change its electrical resistance with changes in R.H., and (4) the ability of a hygroscopic aluminum oxide film to change its electrical resistance with changes in R.H. There are various types of Psychrometers available, too, and these in general depend on determining the difference between "wet-bulb" and "dry-bulb" thermometer thermometer readings to indicate the R.H. of the gaseous environment. There are still other types which depend on electrolyzing the water in the gas stream in order to determine it concentration and thus the R.H. Still others depend on cooling the gas to determine its "dew point," a point which may be related to R.H. with suitable tables. However, all these devices are either mechanically complex, require special manipulation in order to get a reading, require external power, or are delicate in nature. Though these limitations are generally tolerable, there is an acute need for what might be termed a "secondary hygrometer," one easily read, rugged, and independent of external power to serve as a warming device in case the complex devices malfunction. For humidity control is vital in an advanced civilization and great damage may occur if it fails.

There exists a simple, visual type of hygrometer based on the fact that certain cobalt compounds change color from blue to red as the humidity rises. This device is widely used of necessity. But it is very difficult to judge R.H. with any precision using this technique because of the subtle color shifts. Further, the change is of an unobtrusive nature and thus unsuitable for serving as a visual alarm.

Accordingly, one of the objects of the present invention is to provide a visual-type hygrometer in which a number of delineated areas change sequentially from blue-black to brilliant white (or vice versa) as the R.H. rises.

Still another object of the invention is to provide a visual humidity alarm in which a relatively large area changes from blue-black to brilliant white (or vice versa) as the humidity varies from some desired range. In such a device suitable warning legends may appear to the viewer after the humidity has deviated from the desired range.

Another object of the invention is to provide a visual means of determining gas flow patterns in ducts, hoods, etc. by allowing suitably humidity gas to impinge on R.H.-sensitive birefringent crystals deposited on a substrate sandwiched between a perforated, spatially separated, polarizer and analyzer.

Another object of the invention is to provide a special type of hygrometer which can be used as a visual-type thermometer. Delineated areas, for example, may change sequentially from blue-black to brilliant white (or vice versa) as the R.H. falls (in response to temperature rise) in a sealed system having a selected absolute moisture content.

As a variant of this, if an R.H.-sensitive compound which is birefringent at high humidities but non-refringent at lower humidities, is deposited on a suitable substrate and this is sealed into a double-pane window of the type used for insulating purposes, and the whole placed between crossed polarizers, a temperature-sensitive system is obtained. When an appropriate absolute moisture content is sealed in, if direct sunlight falls onto the system the temperature rises, the R.H. drops sufficiently, birefringence ceases, and the system no longer transmits appreciable light.

Another object of the invention is to provide a visual-type moisture tester in which delineated areas change sequentially from blue-black to brilliant white (or vice versa) to indicate the R.H. of the system and thus, secondarily, the moisture content of the material being tested, as paper, tobacco or wood.

Additional objects and advantages of the visual-type hygrometer of the present invention will be apparent to one skilled in the art to which it pertains and upon reference to the following disclosure of several preferred embodiments thereof, and which are illustrated in the accompanying drawings, in which.

Figure 1:
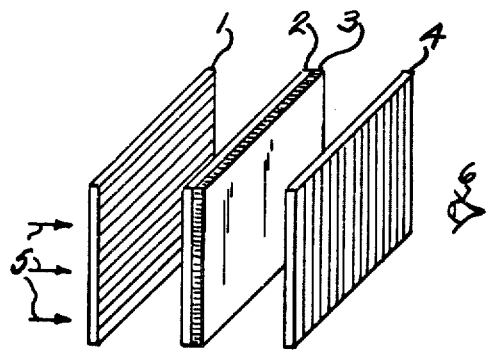
FIG. 1 is a view of a typical transmission-type system.

In a representative embodiment of the visual-type hygrometer of the present invention shown in FIG. 1, a light beam from light source 5 which may be a window, a tungsten lamp, a flurescent lamp, etc. passes through Polariod polarizer 1 where the light beam is polarized. The beam then passes through transparent or translucent substrate 2 which may be glass or some isotropic plastic such as cellulose triacetate, on which is deposited crystal layer 3. The beam passing through 2 and 3 then encounters Polaroid analyzer 4 whose polarizing axis is usually at right angles to the polarizing axis of 1 so as to result in what is generally termed a "dark field."

If the coating 3 on substrate 2 is in its non-birefringent mode, little light passes through analyzer 4 and the system appears "dark field" to viewer 6. However, if the humidity changes sufficiently, coating 3 becomes birefringent. When a light beam enters a birefringent or, as it is sometimes called, double refracting material, it is divided into two components, one defined as an extroadinary ray and the other as an ordinary ray, each vibrating in a direction at right angles to the other and traversing the birefringent material with a different velocity to thereby introduce a phase difference therebetween. As said beam is thereby resolved into two components, one of which is retarded with respect to the other, said beam is generally referred to as being elliptically polarized. The two components emerging from the birefringent material and entering the second sheet of polarizing material 4 are resolved into one plane-polarized beam again. But a phase difference has been introduced between the two parts of this same beam, and so the necessary conditions for interference are present. With a white light source brilliant colors will emerge from analyzer 4 if the coating 3 crystallizes in large crystals. If the crystals are very small there is a mixing of colors and the crystal mass appears white. But in either case the field which was previously a blue-black passing very little light now glows brilliantly.

It is known, of course, that a single molecule of a compound such as tetraalkali 3,3',4,4' benzophenone tetracarboxylate is not birefringent of itself as represented by the aforementioned U.S. Pat. No. 3,510,513. For example, in solution the individual molecules are not birefringent and this fact is noted below. During the drying process molecules of some compounds may be drawn together to form a glass-like amorphous solid or to form crystals of the cubic system. Neither of these two forms is birefringent.

But in contrast as will be more fully explained herein, polar forces may cause association of molecules of other compounds in such a way that the microcrystals formed (the so-called unit cell of crystallographers) are birefringent. That is, the molecules may assemble in such a way that the crystal has more than one index of refraction. It is such birefringent crystals which are useful for signalling, for example with polarized light as is discussed above.

The hydrated alkali salts of 3,3',4,4' benzophenone tetracarboxylic acid and their complexes to be discussed subsequently are labile, readily drying at low humidities to a form containing little or no water. Then, as the relative humidity (RH) rises, an RH is reached where, depending on the ratio of the alkali metal cations present, the constituent molecules hydrate and a birefringent crystal forms. It is these solid, hydrated, birefringent crystals of alkali metal 3,3',4,4' benzophenone tetracarboxylates or their complexes which signal and are the entities of the present invention.

As noted above, under certain conditions polymorphism or polytypism phenomena may result in the formation of solid, hydrated, birefringent crystals in which the constituent alkali metal 3,3',4,4' benzophenone tetracarboxylate molecules are organized in a somewhat different way from the organization secured under conditions where no nucleating agents are present. As indicated, these irreversible birefringent forms can be valuable and effective signalling agents. So whether a structure is sought which is characterized by reversible birefringent/nonbirefringent changes or by irreversible birefringent changes depends on the application intended. The key matter is the appearance of a crystalline, birefringent, hydrated signalling form at an appropriate R.H.

There are many crystals which form hydrates and which even deliquesce. Certain of these materials, which are exemplified by calcium chloride and certain forms of calcium sulfate, are used widely as industrial desiccants. For this reason the amount of water which they will take up in passing from the less hydrated to the more hydrated (or even deliquescent) stage is a matter of great economic and industrial importance. However, the hydrates of this invention are of value because of their ability to signal, not because of the amount of water which they can take up. Further, as has been noted, infinitely variable isomorphous series comprising mixtures of different alkali metal cations combined with the 3,3',4,4' benzophenone tetracarboxylate radical allow signalling over a very wide RH range without in any way being usefully related to the exact amount of water of hydration being present in any particular salt mixture at the trigger point. Thus, the amount of water of hydration present in these compounds at the signalling point is not considered pertinent.

Figure 2:
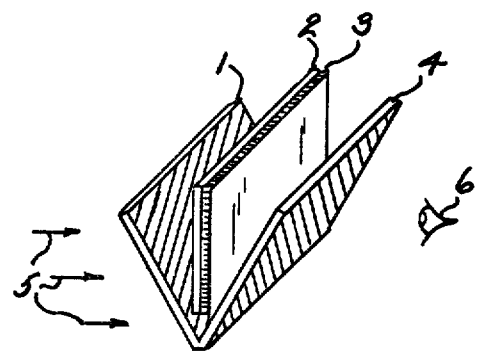
FIG. 2 is a view of a transmission-type system using a single piece of polarizing material.

FIG. 2 is essentially the same as FIG. 1 but better adapted to mass production in that a single piece of polarizing material is folded at 45° to its polarizing axis. This forms two leaves 1 and 4 whose polarizing axes are at right angles to one another and so create a "dark field" condition when the viewer 6 interposes the folded layers between him and light source 5. A substrate 2 coated with R.H.-sensitive layer 3 is then inserted to create a R.H.-responsive sandwich. Or, if desired, the layer 3 may be coated on one or both inner surfaces of 1 and 4 so as to eliminate the need for a separate substrate.

Figure 3:
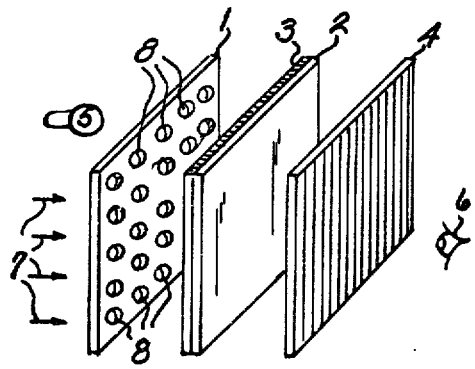
FIG. 3 is a view of a transmission-type system designed to most efficiently check the R.H. of a gas stream normal to the polarizer and analyzer.

FIG. 3 typifies a transmission-type system useful for checking the humidity (and uniformity of moisture and/or air distribution) of air emerging from ducts. Air stream 7 passes through apertures 8 pierced in Polaroid polarizer 1 illuminated by lamp 5. The air stream then encounters R.H.-sensitive layer 3 coated onto substrate 2. Viewer 6 scans the system through analyzer 4 to determine uniformity of birefringence.

Figure 4:
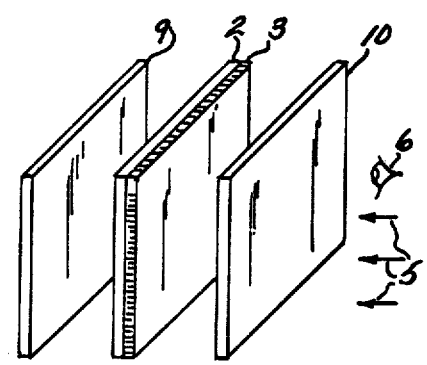
FIG. 4 is a view of a typical reflection-type system.

FIG. 4 typifies a reflection-type system in which light beams from a source 5 pass through polarizer 10 where they are polarized. They then pass through a R.H.-sensitive layer 3 coated on substrate 2 to the polarization-conserving mirror 9. The mirror reflects the beam back through the Polaroid 10 which now serves as an analyzer. As a variant of this system a circular polarizer may be used for 10 in place of the usual linear polarizer. Then, when the coating 3 non-birefringent, no light will be reflected back through 10 because the circular polarizer has polarized the beam to a "right-handed" or "left-handed" helix form which cannot pass back through the circular polarizer 10. When coating 3 becomes birefringent, the polarization form of the light that is reflected from the mirror is altered and the returning light passes through the polarizer 10.

The hydrometers described may be used as "moisture meters" as well by simply taking care to enclose the hygrometer with the hygroscopic material whose moisture content is to be measured so that the salts may come to equilibrium with the atmosphere over the hygroscopic materials. Thus, a hygrometer may simply be buried in a product such as a grain and allowed to remain there long enough to equilibrate with the grain. In other cases, the product whose moisture content is to be tested is temporarily sealed into a container with the hydrometer until equilibrium is reached. In each case, of course, a chart must be prepared for the particular product relating R.H. over the product to the moisture contained in the product at that R.H. This chart is then consulted, knowing the R.H. reading, to determine the product's moisture content.

Figure 5:
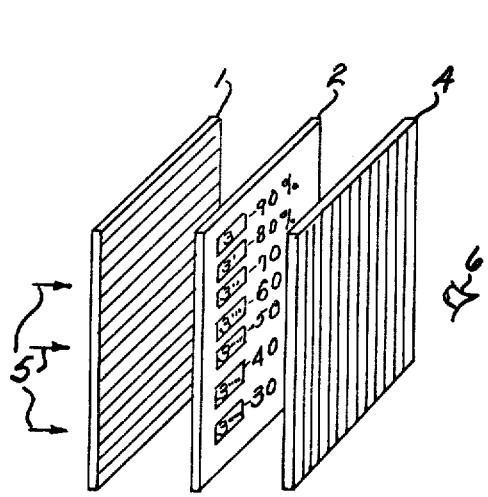
FIG. 5 is a view of a typical transmission-type system using sequential R.H. series of placques.
Figure 6:
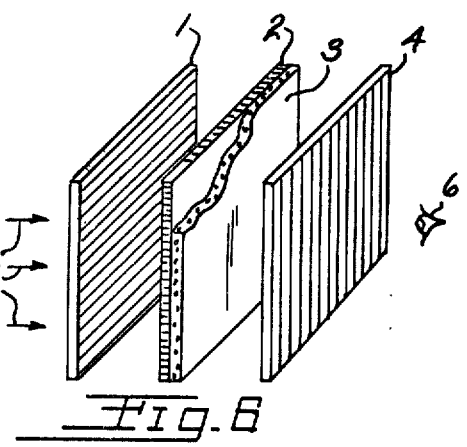
FIG. 6 illustrates another embodiment of typical transmission type such as shown in FIG. 1.

The substrte on which the R.H.-sensitive layer is deposited may be of a smooth material such as isotropic glass if the device is to be operated in the horizontal plane. However, when the device is vertical, the R.H.-sensitive layer, when it is in the liquid condition, may drain to the bottom of the plate under the influence of gravity. Under such circumstances, since roughening of the surface generally allows the solutions used to wet the substrate more thoroughly, placques may be sand-blasted or etched into the substrate to give anchorage to the solutions and prevent their moving downwardly across the poorly wetting smooth surface, Such a unit is shown in FIG. 5 where the coatings, 3, 3', 3", etc. are applied to etched areas on substrate 2.

To further control drainage problems the solutions of R.H.-sensitive compounds may be deposited in quite small areas, of circular shape, for example, either on smooth or etched spots on the substrate. These "droplets" may be "printed" onto the surface, for example, or they may be deposited by spraying through apertures in a mask over the substrate. The droplets of solution, analogous to the dots which comprise "half-tone" pictures, may be arranged to form placques, R.H. legends, warnings, etc.

Other methods may be used to create effective visual presentations of the R.H.-sensitive salt layers. Thus, very small glass beads of the type used in manufacturing reflective signs may be cemented to a substrate with a suitable cement, as for example an epoxy. The beads are spaced closely and insufficient adhesive is used to fill the interstices. Thus, a large number of small cavities are formed between the beads. R.H.—sensitive salt solutions may be deposited in these davities to form visually effective displays as water evaporates and crystallization occurs.

R.H.-sensitive salt solutions may also be deposited in narrow channels or holes engraved into such substrates as transparent acrylic polymers. Such channels serve to hold the salt in its liquid form yet make effective displays when moisture has evaporated and birefringent crystals have formed. The channels may form numbers indicating the particular R.H. range of the salt filling the channels or may form rectangular display panels, etc.

The solutions of R.H.-sensitive compounds are desirably compounded with non-hygroscopic wetting agents to lower their surface tension so that they wet the chosen substrate. Since salts or other polar compounds are often selected for use as R.H.-sensitive compounds, the wetting agents are most suitably of a non-ionic form. Further, so as to secure effective but controlled wetting of the substrate, sufficient wetting agent is desirably compounded into the solution to obtain a surface tension near but not below the Critical Surface Tension of the substrate. That way a small contact angle is secured but wetting does not proceed spontaneously across the entire surface so as to cause drainage problems due to gravity.

Though generally good wetting is desired, in special cases poor wetting may be advantageous to create warning devices. Thus, a solution of an R.H.-sensitive compound having a naturally high surface tension may be sprayed onto a substrate in such a concentrated form that it dries almost immediately at the temperature and/or R.H. present under spraying conditions. This R.H.-sensitive film on its carrier substrate may then be displayed in typical transmission- or reflection-type hygrometers where an evenly illuminated, birefringent surface is maintained so long as the R.H. remains below the critical point typical of the particular compound. Above the critical R.H., the hygroscopicity of the film removes moisture from the air and the birefringent crystals dissolve. The high surface tension of the solution then causes it to pull together into droplets. Thus, even if the dangerously high R.H. is subsequently lowered, a simple visual inspection of the film will reveal by the presence of droplets that the danger point was indeed passed. This type of signal is especially important, for example, in the storage of packaged equipment outdoors in the tropics where wide temperature variations can bring wide R.H. fluctuations inside the sealed package. Near the end of the life of enclosed dehydrating agents such as silica gel, the R.H. within the package can appear safely low at elevated daytime temperatures but it is actually dangerously high at lower night temperatures. The device just described maintains a round-the-clock watch for dangerously high humidities.

Compounds may be of the type which pass from a nonbirefringent state to a birefringent state as the R.H. rises. One mechanism by which this can happen is believed to involve the formation of unstable hydrates which are birefringent. The birefringent hydrate is stable above a particular R.H. yet converts readily to a non-birefringent material of anhydrous form or of a lower degree of hydration as the R.H. drops below the critical moisture concentration. A good example of such a material is the tetrapotassium salt of 3,3'-4,4' benzophenone tetracarboxylic acid which becomes birefringent at approximately 46% R.H. It continues birefringent until the R.H. rise to the place where deliquescence causes solution of the crystals with abrupt termination of birefringence. This occurs at approximately 65% R.H.

There are two basic types of compounds which are useful as the active agents in temperature- or R.H.-sensitive devices. The first type includes those compounds which are birefringent in the hydrated state but non-birefringent when anhydrous or when the water or hydration has dropped below a critical point.

There are a large number of compounds which exhibit birefringence when viewed between a polarizer and analyzer. Many of these compounds are hydrated as well. However, most of these materials are impractical for use as R.H. or temperature sensors because the water of hydration is bound so tightly into their structure. Once hydrated formations have been created, as from solution, water may be slowly driven out, but usually only through the use of impractically low humidities and excessively high temperatures. This, unfortunately, usually destroys the mechanical integrity of these tightly organized structurea and a powder forms. That is, each crystal unit is so disrupted that it cannot easily be restored to its original coherent birefringent form by simply raising the relative humidity to the original level at which the hydrated material was stable. Thus, such polarized light devices as have been described here have not been feasible.

I have discovered a new class of compounds which make possible such visual sensors. I do not intend to be bound by theory, but it appears that films of such substances are characterized by submicroscopic openness of structure which allows water to readily move in and out of the system. That is, the hydrated, birefringent structure rapidly and easily forms under appropriate conditions, yet the anhydrous or less hydrated non-birefringent form is readily reconstituted when earlier conditions are reestablished.

The materials are the salts of relatively symmetrical compounds characterized by having at least two rings bearing carboxyl, hydroxyl, or sulfonic groups. The rings are jointed by a bond or bonds of a type which, it is hypothesized, allow ring rotation around the bond so that bulky, nonplanar structures result. Ordinary planar molecules readily form compact, highly organized structures. However, it is believed that the molecules of this new class of compounds form crystal structures quite open to the passage of water molecules. In particular, these compounds comprise the alkali salts, pure or mixed, of molecules consisting of at least two rings bearing carboxy, hydroxy, or sulfo groups as substituents. The substituents may be on the same or separate rings.

Such groups as —OK, —OORb, and —SO$_3$Na furnish ions to hydrate, and these individual groups are highly polar. If such groups were asymmetrically distributed, molecules would result which had high dipole moments. On the other hand, even the most polar of groups, if balanced by other polar groups, may comprise part of a molecule which as a whole is substantially non-polar. By symmetrically distributing around the molecule polar groups possessing ions which can hydrate, I theorize that a structure is formed which can rather readily hydrate or dehydrate, for its individual molecules are not drawn into tight, intermolecular orientation by polar effects.

Summarizing, molecular configurations are not easily or precisely established. However, a wide range of molecular shapes can be expected, depending on the general configuration and the type and placement of substituent groups, ranging from molecules in which the rings are almost planar (little bulkiness) to those in which the rings are highly non-planar (high bulkiness). Although not wishing to be bound by theory, it is believed that water of hydration moves in and out of molecular aggregates of the former molecules which can be tightly packed with considerably more difficulty than with the latter. Putting it another way, a relatively low driving force (such as low water vapor pressure) is adequate to move water to the alkali metal ions of an open structure salt, everything else being equal, as compared with a tight structure.

The best compounds that are birefringent at a first relative humidity and non-birefringent at a second relative humidity are alkali metal salts of 3,3',4,4'-benzophenone tetracarboxylic acid and alkali metal salts of 1,1,3-trimethyl-5-carboxy-3 (p-carboxyphenyl) indan. The molecular structure of each is given below along with the approximate relative humidity at which certain alkali metal salts thereof become birefringent:

Alkali Metal Salts of
1,1,3-Trimethyl-5-carboxy-3-(p-carbosyphenyl) Indan

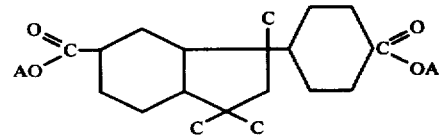

where A = an alkali metal
Relative Humidities of the Alkali Metal Salts:
Li$_2$ salt = 74%
Na$_2$ salt = 62%
K$_2$ salt = 53%
Rb$_2$ salt = 45%

Alkali Metal Salts of 3,3',4,4' Benzophenone Tetracarboxylic Dianhydride

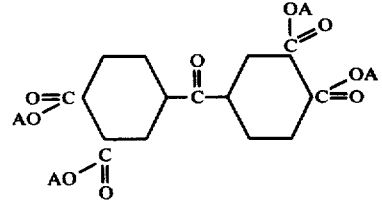

where A = an alkali metal

Relative Humidities of the Alkali Metal Salts:
Li$_4$ salt = 68%
Na$_4$ salt = 57%
K$_4$ salt = 43%
Rb$_4$ salt = 20%

In general the alkali metals include sodium and potassium which are preferred for convenience and economy, as well as lithium, rubidium and cesium.

Although not as good as the above described alkali metal salts of the indan and benzophenone compounds, a preferred composition is the alkali metal salts of mapthochrome green, the disodium salt thereof being birefringent at a relative humidity of about 84%.

Other suitable compositions are alkali metal salts of 1,1' binaphthyl 8-8' dicarboxylic acid. The Na$_2$ salt begins to display birefringence at about 53% relative humidity at 70° F. The sodium salt was stroked to induce crystallization and after repeated cycling, the birefringence tended to become irreversible. The K$_2$ salt did not crystallize so that there was no observation.

Other suitable compositions are alkali metal salts of benzophenone 4,4'-dicarboxylic acid, the sodium salt beginning birefringence at about 96% relative humidity, the potassium salt beginning birefringence at about 85% and the rubidium salt beginning at about 75%.

The following list contains suitable alkali metal salts of compounds that were tested and indicates the approximate temperature in °F. below which the alkali metal salt is birefringent:

| Compound | Alkali Metal | Temperature °F. | Remarks |
| --- | --- | --- | --- |
| 3,3-Bis-(4-hydroxyphenyl) oxindole | K$_2$ | 254 | Was stroked to induce birefringence which became irreversible after a few cycles. |
| 2,4' Benzophenone dicarboxylic acid | K$_2$ | 176 | Glassy film first forms (non-birefringent) which subsequently crystallizes, making observation possible. |
| o-Benzoyl benzoic acid | K | | |
| | Na | 300 | No dehydration at 300° (no cessation of birefringence) |
| | Rb | | No dehydration at 300° (no cessation of birefringence) Films difficult to observe because glassy film crystallizes with difficulty. Considerable background birfringence present with K salt above 300° F. |
| 2,4,4'-Trihydroxy benzophenone | K$_3$ | 220 | Required thin film for dehydration to occur. |
| 2-Hydroxy-4-,methoxy-benzophenone-5-sulfonic acid | K$_2$ | 275 | No stroking required to induce birefringence |
| 2-Hydroxy-4-methoxy-benzophenone | K | 122 | Stroking required to induce birefrinence of film. |
| 2,2'-Dihydroxy-4,4' dimethoxy benzophenone | K$_2$ | 250 | |
| 2-(-hydroxybenzoyl)-Benzoic acid | K$_2$ | 221 | |
| 2,2' Dihydroxy benzophenone | K$_2$ | 250 | |
| o-Hydroxybenzophenone | K | 113 | |
| 4,4' Dihydroxybenzophenone | K$_2$ | 260 | |
| Chlorobenzoyl benzoic acid | K | 290 | Tends to form considerable background birefringence on cycling. |
| 2,4 Dihydroxbenzophenone | K$_2$ | | No dehydration (no cessation of birefringence) at 300° F. |
| Sodium 2,2'-dihydroxy-4,4'-dimethoxy-5-sulfobenzophenone | Na | | No cessation of birefringence at 300° F. |
| | NaK$_2$ | | No cessation of birefringence at 300° F. |
| 2,2',4,4'-Tetrahydroxy benzophenone | K$_4$ | | No dehydration (no |

-continued

| Compound | Alkali Metal | Temperature °F | Remarks |
|---|---|---|---|
| Phenol red | K | 150 | cessation of birefringence at 300° F.) |
| p,p' Biphenol | $K_2$ | 290 | Thin layers required for dehydration and cessation of birefringence. Residual birefringence persists after major dehydration. |
| o,o' Biphenol | $K_2$ | 194 | |
| 2,2' Diphenic acid | $Rb_2$ | 240 | |
| | $K_2$ | | No dehydration (no cessation of birefrinence apparent at 300° F.) |
| 4-Biphenylcarboxylic acid | K | | No dehydration (no cessation of birefringence at 300° F.) |
| 1,1'-Bi-2-naphthol | $K_2$ | | No dehydration (no cessation of birefringence at 300° F.) |
| 4,4' Biphenyldisulfonic acid | K | | No dehydration (no cessation of birefringence at 300° F.) |
| | $Rb_2$ | | No dehydration (no cessation of birefringence at 300° F.) |
| Phenolphthalein | K | 169 | In conc. soln. approx. 100% more KOH required than theo. for $K_3$ salt to form salt capable of birefringence. Even then stroking of film required to align molecules and so develop birefringence. |
| Bisphenol A | $K_2$ | 266 | Tended to gradually form birefringent crystals which would no longer dissociate on heating. |
| Bishydroxy coumarin, (3,3'-methylenebis [4-hydroxy coumarin]) | $K_2$ | 150 | |
| | $K_4$ | 150 | |
| Methylene disalicyclic acid | $K_2$ | 255 | Tended to form glassy film. |
| | $K_4$ | 255 | |
| Benzilic acid | K | | No dehydration at 300° F. |
| | Rb | | Strong crystal formation of high birefringence. |
| Diphenyl acetic acid | K | 290 | Slow dehydration with strong residual background birefringence. |
| Dichlorophene 2,2'-methylenebis -(4-chlorophenol) | $K_2$ | | No dehydration at 300° F., i.e., no cessation of birefringence. Highly crystalline birefringent film. |
| 6,6 Bis-(p-hydroxyphenyl) -3-(1-hydroxy 1-methyl ethyl)-heptanoic acid gamma lactone | $K_3$ | | No dehydration at 300° F. |
| Hexachlorophene, [2,2' methylenebis -(3,4,6-trichloro -2-hydroxyphenyl) methane] | $K_2$ | | No hydration at 300° F., i.e., no |

-continued

| Compound | Alkali Metal | Temperature °F. | Remarks |
|---|---|---|---|
| Diphenolic acid | K hd 3 | | cessation of birefringence. No dehydration at 300° F., i.e., no cessation of birefringence. |
| Pamoic acid | | | When both-COOH or both-COOH plus-both -OH's neut., no dissociation observed at 300° F., i.e., no essation of birefringence. Salts tended to form glasses which crystallized with great difficulty. |
| 2,6-Divanillylidenecyclohexanone | $K_2$ | 254 | |
| 4',5,7-Trihydroxy flavenone | $K_3$ | | No dehydration (no cessation biref.) at 300° F. |
| 4,4' Oxydiphenol | $K_2$ | | No dehydration (no cessation biref.) at 300° F. |
| 2,2'-Thiobis (4,6-dichlorophenol) | $K_2$ | 290 | Heavy residual birefringence after 290° reached. |
| 2,2' Dithiodibenzoic acid | $K_2$ | | No crystallization. |
| | $Na_2$ | 230 | Crystallization only slowly occurring. Heavy residual birefringence after 230° F. reached. |
| Dihydroxy-diphenyl sulfone | $K_2$ | 240 | Residual birefringence after 240° F. reached. |
| 5,5 Thiodisalicyclic acid | $K_2$ | | No dehydration (no cessation birefringence at 300° F. |
| | $K_4$ | | Same as $K_2$ Salt. |

There is another factor having to do with the choice of molecular configurations which is of importance in the design of R.H.- or temperature-sensors having maximum industrial utility. As noted before, it is believed that the substituent groups contribute to positioning the rings in bulky, open configurations, the degree of bulkiness depending in part on the substituents. However, though the molecules may be unorganized when dissolved in the solution from which they are to be deposited, powerful intermolecular forces come into play as water evaporates and the molecules are forced more closely together. Observation suggests that some molecules of the type found effective are able to totally resist being forced into close, tight molecular groupings during evaporation of water. For the dehydrated material shows no birefringence after thousands of dehydration-hydration cycles. Other molecules, however, develop what might be termed a "background-haze," a partial birefringence in the dehydrated form when observed in polarized light. Sometimes this haze develops immediately, sometimes it develops on repetitive cycling through the phases of "dehydrated solid/hydrated solid/dehydrated solid."

It is thought that this haze develops because a small proportion of the molecules succumb to intermolecular organizing forces since the rings have a considerable degree of rotational freedom in spite of the effect of the substituent groups. Thus, chance may bring some molecules into a tightly organized, birefringent microcrystal which is not readily disrupted even by deliquescence. As noted before, some molecular structures are entirely free of this hazing tendency and these are preferred for use in indicating devices. For though the presence of background haze does not prevent those compounds from being used as indicators, the effect is more dramatic when the field changes from blue-black to great brilliance or vice versa.

This tendency of certain molecular species to succumb to organizational forces and so pass from the isotropic to the birefringent state under particular conditions may be put to valuable industrial use. In particular, it has been found that some species (for example, the alkali salts of 1,1,3-Trimethyl-5-carboxy-3-(p-carboxyphenyl)indan as recorded in Table 1) are highly stable in the anhydrous (or minimum hydration) state, which is characterized by its isotropic nature when viewed between crossed Polaroids. However, when the ambient R.H. passes the critical leval at which the compound hydrates and becomes birefringent, organizational forces begin to operate. In a very limited time, varying from a few hours to a couple of days, a new essentially irreversible birefringent crystal structure develops. Thus, even though the R.H. subsequently drops below the critical R.H. at which birefringence originally began, the film remains permanently birefringent.

This "memory" feature of certain molecular structures is invaluable. For, as noted elsewhere, there are many industrial areas where cyclical changes in R.H. occur and where it is desired that critical humidities (as pounds are shown in Table 1, together with the % R.H. at which birefringence begins if the R.H. is rising, or terminates if the R.H. is dropping, in the case of low mass deposits of the type used in these sensors. Since the alkali metals form isomorphous series of compounds, the R.H. response of the particular hygrometric series is controlled by using varying mol ratios of alkali metals as the cations.

TABLE 1

| R.H. at which birefringence begins | Birefringent, Labile Hydrates Having Sequential R.H. Response | | |
|---|---|---|---|
| | Anion | Cation A/B | Mol % Cation A Mol % Cation B |
| 74.26 | 1,1,3-Trimethyl-5-carboxy-3-(p-carboxyphenyl)indan | Li/- | 100 |
| 71.7 | " | Li/Na | 75/25 |
| 70.2 | " | Li/Na | 50/50 |
| 67.2 | " | Li/Na | 25/75 |
| 63.1 | " | Na/- | 100 |
| 62.5 | " | Na/K | 75/25 |
| 60.6 | " | Na/K 50/50 | |
| 57.6 | " | Na/K | 25/75 |
| 53.2 | " | K/- | 100 |
| 50.7 | " | K/Rb | 75/25 |
| 49.5 | " | K/Rb | 50/50 |
| 47.3 | " | K/Rb | 25/75 |
| 45.1 | " | Rb/- | 100 |
| 69.4 | 3,3',4,4' Benzo-phenone Tetracarboxylic Dianhydride | Li/- | 100 |
| 67.5 | " | Li/Na | 75/25 |
| 66.0 | " | Li/Na | 50/50 |
| 62.5 | " | Li/Na | 25/75 |
| 58.6 | " | Na/- | 100 |
| 55.9 | " | Na/K | 75/25 |
| 53.2 | " | Na/K | 50/50 |
| 49.8 | " | Na/K | 25/75 |
| 43.0 | " | K/- | 100 |
| 39.1 | " | K/Rb | 75/25 |
| 32.2 | " | K/Rb | 50/50 |
| 25.0 | " | K/Rb | 25/75 |
| 18.0 | " | Rb/- | 100 | that at which fungi development begins) are not exceeded. The compounds just described are excellent as inexpensive visual alarms, inactive indefinitely below the critical R.H., but ready to respond promptly and to hold their message for the next viewing observer.

There is another factor besides the intrinsic bulkiness of the cyclic organic structures which affects the openness of the final film. This has to do with the bases selected to neutralize acidic molecules. For since the atomic volumes and structures of the different cations selected to combine with the organic molecules described vary, the spatial arrangement of the total molecules of which they come to comprise a part also is affected. This in turn modifies how the molecules join other similar molecules to form a macro-structure. Thus, various cations may be selected depending on the nature of the opposite ion of high bulkiness and complexity. By judicious selection of anions and cations, compounds can be prepared which hydrate and dehydrate with varying degrees of ease. This, in turn, means that substances are available for use as sensitive agents to indicate visually, when the compounds are deposited on suitable substrates and viewed with polarized light, the existence of various relative humidity levels or temperatures.

At a certain temperature, what decides whether a particular compound gains or loses water is the pressure of water vapor around the molecule. Most hygrometers are used within a relatively narrow temperature band of perhaps 40° to 95° F. in areas where the R.H. is relatively high. Thus, structures are needed in which the water of hydration is loosely bound. Suitable com- Industrially, besides the need for simple hygrometers, there is a need for simple, visual thermal indicators which can be of large surface area for high recognition value. These indicators may be used to guard thermally-sensitive equipment, to indicate through a viewing aperture the temperature of gases in spaces such as ducts and environmental rooms, to indicate temperature distribution over relatively large areas as in the design of electric irons and hotplates, etc. Such indicators and alarms are usually required to operate at somewhat elevated temperatures, in particular above 100° F. For such applications, indicating compounds are desired in which the water is relatively tightly bound since the pressure of water vapor in open air which has been heated to a high temperature is quite low. The rapid drop in R.H. as the temperature is raised is shown in Table 2.

TABLE 2

| % Relative Humidity vs. Air Temperature (70 grains moisture/lb. dry air) | | | |
|---|---|---|---|
| Temp., °F. | % R.H. | Temp. °F. | % R.H. |
| 70 | 65 | 150 | 6 |
| 80 | 46 | 160 | 5 |
| 90 | 34 | 170 | 4 |
| 100 | 25 | 180 | 3 |
| 110 | 18 | 190 | 2.5 |
| 120 | 14 | 200 | 2.0 |
| 130 | 10 | 210 | 1.6 |
| 140 | 8 | 220 | 1.4 |

Essentially, because of the relatively broad limits which typify simple alarm systems, the ambient relative humidity, which indicates the vapor pressure of water (or the back-pressure which is operating to prevent the hydrate from dissociating), can be considered as a constant at relatively high temperatures. Thus, one can measure the temperature at which various hydrates cease birefringence with the knowledge that variations of ambient R.H. (at room temperature) will have little effect on the temperature at which birefringence ceases. Table 3 lists various compounds together with the temperature at which birefringence ceases.

TABLE 3

Compounds and Temperature at Which Birefringence Ceases

| Compounds | Temp., F. |
|---|---|
| Potassium Salt of o-Hydroxybenzophenone | 113 |
| Potassium Salt of 2-Hydroxy-4-methoxy-benzophenone | 122 |
| Potassium Salt of Phenol red | 151 |
| Potassium Salt of 2,4' Benxophenonedicarboxylic/acid | 176 |
| Potassium Salt of 0,0'-Biphenol | 194 |
| Potassium Salt of 2-(p-Hydroxybenzoyl)-benzoic acid | 221 |
| Potassium Salt of 2,2'-Dihydroxy-4,4'-dimethoxy-benzophenone | 250 |
| Potassium Salt of o-Benzoyl benzoic acid | 300 |

Other compounds may be used advantageously in assembling a suitably responsive series. Among the compounds whose alkali metal salts are appropriately responsive at various temperatures are the following:

| | |
|---|---|
| p,p Biphenol | 2,2' Dihydroxybenzophenone |
| 2,2' Diphenic acid | 4,4' Dihydroxybenzophenone |
| Phenolphthalein | 2-Hydroxy-4-methoxy-benzophenone 5-sulfonic acid |
| Bisphenol A | |
| | 3,3-Bis-(4-hydroxyphenyl)-oxindole |
| Bishydroxycoumarin | |
| Methylene disalicyclic acid | 2,6-Divanillylidenecyclo-Hexanone |
| 2,4,4'-Trihydroxy-benzophenone | |

These labile compounds can also perform the industrially useful task of serving as detectors of various types of radiation. Thus, either pure compounds or those compounded with dyestuffs, for example, to make them highly absorbent to a selected band of radiation, can serve as radiation detectors. Further, to increase the sensitivity the compounds may be mounted on substrates which absorb the radiation to be visually detected.

A wide variety of materials absorb acoustical and electromagnetic radiation of various wavelengths. Usually a portion of the absorbed radiation is converted to kinetic energy resulting in a rise in temperature of the material and its surroundings. Infra red heating panels and microwave heating ovens typify industrial applications of varying radiation bands. As part of the intelligent application of various types of radiation, it is desirable to rapidly determine the distribution of radiation, whether it is emanating directly from an infra red panel or an ultrasonic cleaning tank transducer, or perhaps is emitting from a distant radiation source and focused by a radiation-transmitting lens. For such detection large, easily observed radiation detection panels are most useful. Very much as with a humidity sensor, birefringent, highly labile hydrates may be disposed on a suitable substrate between crossed polarizers. As the compounds and/or substrate absorb radiation, the temperature of the materials and the overlying gas rises with an accompanying dissociation of the hydrates and cessation of birefringence. To make the system more sensitive, the polarizing sheets, sensitive compound, and substrate may comprise a sealed system. The R.H. of the encapsulated gas is preferably selected to be close to the critical humidity at which birefringence ceases at the ambient temperature of operation. Thus, only a small amount of absorbed radiation will cause a temperature rise, reduction of the R.H. of the gas, evaporation of the water of hydration and cessation of birefringence. Less sensitive than the system described is one based on the appearance of birefringence in compounds which had ceased birefringence because they had deliquesced.

Many variants of these practices are possible, of course. Thus, referring to FIG. 1 again, flexible substrate (2) on which is deposited crystal layer (3) might be in roll form so that the hydrated crystal layer and substrate might unroll under and close to a heated, laterally-moving stylus in a recording instrument. Thus, a narrow line of non-birefringent, dehydrated crystals would form under the heated stylus. On passing between polarizer (1) and analyzer (4) a "curve" would be observed to have been drawn by the stylus. This curve will be permanent if the substrate/crystal is stored below a certain critical R.H. But the curve may be obliterated and the film used again by simply exposing the film to a high humidity to rehydrate the previously dehydrated crystals.

For use in the applications described I have discovered a vital type of addition agent for compounding with the materials described. This type of agent includes a number of inorganic compounds of high surface area having little or no intrinsic birefringence. When these materials are added to solutions of the active organic compounds already described, a new sensitivity to changes of humidity is observed in the dried droplets or films deposited from such suspensions. This is of great industrial importance since it is often essential to rapidly ascertain shifts in R.H. Indeed, many mechanical R.H. meter manufacturers state the time in which their devices will move a certain proportion of the way toward a new R.H. reading when the R.H. has shifted. Using these high surface area agents, only a few seconds are required for a sensor film to come to a new equilibrium when the R.H. has shifted. Further, much higher driving force (lower R.H.) is required to dehydrate the films so that birefringence ceases if the high surface area agents are not used. Table 4 shows graphically the new sensitivity contributed by these agents.

TABLE 4

% R.H. at Which Birefringence Ceases (Due to Dehydration) When High Surface Area Compounding Agents Are Used (Rb$_2$ Phenylindan Dicarboxylate is R.H.-sensitive Compound)

| Compounding Agent | Agent Area M./gr. | gr. Agent/ 1 gr. Rb Salt | % R.H. Birefringence Ceases |
|---|---|---|---|
| None | — | — | 42.7 |
| Diatomaceous Earth | Relatively Low | 1.00 | 43.0 |
| Pyrogenic Silica | 200 | 0.30 | 45.2 |
| Pyrogenic Alum. Oxide | 100 | 0.60 | 45.2 |
| Pyrogenic Mixed Silica/ Alum. Oxide (14% Al$_2$O$_3$) | 150 | 0.45 | 46.0 |
| Precipitated Silica | 370 | 0.16 | 46.0 |
| Pyrogenic Mixed Silica/ Alum. Oxide (1.3% Al$_2$O$_3$) | 50 | 1.20 | 51.5 |
| Pyrogenic Mixed Silica/ | | | |

TABLE 4-continued

% R.H. at Which Birefringence Ceases (Due to Dehydration) When High Surface Area Compounding Agents Are Used (Rb$_2$ Phenylindan Dicarboxylate is R.H.-sensitive Compound)

| Compounding Agent | Agent Area M./gr. | gr. Agent/ 1 gr. Rb Salt | % R.H. Birefringence Ceases |
|---|---|---|---|
| Alum. Oxide (1.3% Al$_2$O$_3$) | 80 | 1.00 | 51.5 |
| Pyrogenic Mixed Silica/ Alum. Oxide (1.3% Al$_2$O$_3$) | 170 | 0.50 | 51.5 |

These same compounding agents are additionally useful in that they render the thickness of the deposited sensitive film non-critical. Some types of molecular structures, when deposited in a pure, uncompounded form in thick layers, have been observed to continue in the birefrigent mode when hydrated, even though the humidity was subsequently reduced far below the point at which they should have given up their water. The great thickness (compared with molecular dimensions) apparently stabillizes the system. Use of high surface area compounding agents reduced or eliminated this phenomenon of thickness-dependency. It is theorized that the sensitive molecules distribute themselves over the high surface of the added solids so that, in effect, two-dimensional structures are exposed to the air.

Earlier I stated that there are two basic types of compounds which are useful as the active agents in temperature- or R.H.-sensitive devices. I have now described the first type and the structures required in detail. The second type which is equally useful has already been mentioned. It includes those compounds which are birefringent in the solid state and which deliquesce so that the birefringent crystals cease birefringence due to solution once a critical R.H. has been exceeded. In particular, I have found that the materials which are suitable for use as indicators are those chemical compounds which form birefringent crystals and whose saturated solutions have vapor pressures between 1.0 and 17.5 mm. of mercury at 68° F.

I have further found that those same substances which have little or no birefringence but which possess high surface area are highly useful agents when used with the second type of compound. For once again they greatly improve the sensitivity of the materials to small changes in R.H. As before, they are advantageously mixed with the solution of the sensitive compound before it is deposited on a substrate.

As before, I choose to deposit the active materials in layers, droplets, channels and interstices so that the thickness of the layer does not greatly exceed about 0.1 mm and preferably does not exceed about 0.05 mm. This then insures adequate brilliance of the visual display yet minimizes the time lag due to the diffusion of water into or out of the indicator layer or particles. In general, the thickness of the coating containing the birefringent composition should be at least about 0.001 millimeter and preferably is at least about 0.005 mm.

In use, as the R.H. rises a particle of deposited material absorbs water and finally dissolves. As the R.H. continues to rise the droplet of solution increases in volume but maintains its structural integrity and location on the substrate. As the R.H. decreases, water is given up by the droplet and at the key point birefringence appears again. Thus, when such droplets are disposed for viewing in a polarized light field, they comprise an effective R.H. indicator. A series of compounds may be selected whose birefringence terminates due to dissolution as the R.H. increases. Thus, a typical series can be prepared from the following compounds:

TABLE 5

| % R.H. | Compound |
|---|---|
| 30 | Potassium Salt of Levulinic Acid |
| 40 | Potassium Salt of Phthalic Acid |
| 50 | Potassium Salt of Succinic Acid |
| 60 | Potassium Salt of Adipic Acid |
| 70 | Potassium Salt of 1,2,4,5 Benzenetetracarboxylic Acid |
| 80 | Potassium Salt of Fumaric Acid |
| 90 | Potassium Salt of o-Benzoyl Benzoic Acid |

This happens to be a series of potassium salts, but many other compounds may be used, depending on the R.H. range to be covered. Table 6 shows another series of suitable chemical compounds, selected from sodium and potassium salts for reasons of economy and availability.

TABLE 6

| % R.H. | Compound |
|---|---|
| 35 | Dipotassium Salt of Tetrahydrophthalic Acid |
| 40 | Potassium Salt of Crotonic Acid |
| 46 | Dipotassium Salt of Maleic Acid |
| 50 | Sodium Salt of 4-Chlorophthalic Acid |
| 60 | Dipotassium Salt of Azelaic Acid |
| 65 | Tetrasodium Salt of 1,2,4,5 Benzenetetracarboxylic Acid |
| 73 | Potassium Salt of Glyoxylic Acid |
| 85 | Sodium Salt of Anthranilic Acid |
| 90 | Disodium Salt of Adipic Acid |

Various chemical compounds may be mixed in varying ratios to form mixed crystals which span different ranges from what might be secured if only pure compounds were used. Inorganic compounds such as sodium nitrate may be used, of course, for R.H.-indication as well as organic compounds.

Various additives may be included in the salt solutions to be applied to the carrier substrates. Dyestuffs may be desired to give a particular color to the crystals for purposes of attracting attention. Antifoaming agents may prove useful in minimizing foaming during application of the surface tension salt solutions to the substrate. Various types of thickeners can be helpful, too, in giving a salt solution sufficient viscosity to allow easy "printing" onto appropriate substrates. In this latter case, especially, a material is generally selected—such as an inorganic silicate—which has no birefringence. Thus, the field stays blue-black until crystallization of the sensitive compound occurs. In some instances the thickener may be bifunctional, both thickening the solution and presenting a high surface area to increase sensitivity to R.H. change as discussed elsewhere.

As another method of applying this invention as shown in FIG. 6, it is possible to disperse droplets of solutions of R.H.-sensitive compounds of the type described in non-aqueous vehicles of the type called lacquers and varnishes. These vehicles may then be applied to suitable substrates where, on evaporation of the non-aqueous solvent, the droplets remain encapsulated in the solidified vehicle. If vehicles are chosen having the proper moisture transmission characteristics, the encapsulated may, for example, loose its water to form beirefringent crystals at suitably low R.H.s. As the R.H. rises, the crystals may then draw moisture into the droplet cavity to deliquesce and cease birefringence. Such coated substrates may be placed between polarizing elements to form hygrometers of the type described elsewhere.

The preparation of the highly preferred alkali metal salts of the 1,1,3-trimethyl-5-carboxy-3-(p-carboxyphenyl)indan compound and the 3,3',4,4'-benzophenone tetracarboxylic acid compounds will be described.

To form the indan acid, an appropriate hydrocarbon can be partially oxidized by air oxidation as described in the Towle and Baldwin article "Make Most Aromatic Acids Using Mid-Century Oxidation Process," Hydrocarbon Processing 43 (11), 149 (1964) or by chromic anhydride oxidation as described in an article by Ipatieff et al, J. Am Chem. Soc., 70, 2123 (1948). The Ipatieff et al article describes a general procedure for the preparation of a suitable appropriate hydrocarbon by reacting an olefin such as trimethylethylene with p-cymene in the presence of sulfuric acid or hydrogen fluoride catalysts. U.S. Pat. No. 3,102,135 describes the production of 1-(carboxyphenyl) indane carboxylic acids and this patent, as well as the Towle et al and Ipatieff et al articles, are incorporated by reference.

The preparation of 3,3',4,4'-benzophenone tetracarboxylic acid is described in U.S. Pat. No. 3,078,279 and U.S. Pat. No. 3,297,727 describes methods of obtaining relatively pure benzophenone acid. These patents are incorporated by reference.

In general carboxy substitute diaryl ketones can be prepared from diarylmethanes such as para ditolyl methane by oxidation thereof with air at an elevated temperature and pressure, for example, 90° C. and 45 pounds per square inch gauge, to obtain benzophenone 4,4'-dicarboxylic acid as described in McCracken et al U.S. Pat. No. 3,075,007. A variety of diarylketone carboxylic acids may be prepared by subjecting to oxidation with nitric acid having an initial concentration of about 5 to about 70 percent, at a temperature of about 110° to 350° C. for about one minute to 48 hours a 1,1-diarylalkane represented in general by the following structural formula:

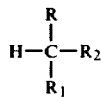

wherein R and $R_1$ are aryl groups carrying as nuclear substituents alkyl radicals having from one to eight carbon atoms and $R_2$ is an alkyl radical having from to eight carbon atoms, the molar ratio of said nitric acid calculated as 100 percent nitric acid, to said diarylalkane being about 8.0 to about 17.0.

The preparation of the alkali metal salts of the previously mentioned benzophenone acid and the benzophenone 4,4'-dicarboxylic acid follows.

Preparation of the Lithium and Potassium Salts of Carboxy Substituted Diaryl Ketones

EXAMPLE I 27.0 grams of benzophenone 4,4'-dicarboxylic acid was agitated in 200 grams distilled water to give a smooth slurry. To this was added 8.4 grams lithium hydroxide monohydrate dissolved in 50 grams distilled water. While agitating, the mass was warmed to 150° F., and held until the suspended material had reacted to form a clear solution of the di-lithium salt, normally about 15 minutes. The solution was then filtered through No. 40 filter paper to remove any traces of dust, ec. and cooled. The solution could be used in this form as a coating agent for glass, cellulose triacetate, polymethylmethacrylate or similar substrates in order to form an R.H.-responsive film after drying. Or if a more sensitive final film was desired, (as described elsewhere), to the filtered solution 17.0 grams of a suitable inorganic compound having a high surface area, as for example a pyrogenic silica, was added and dispersed. A high-shear mixer such as a Waring Blender is suitable for dispersion of the silica. The thickened salt solution can then be used as a coating agent just as the clear filtered solution can be.

EXAMPLE II 35.8 grams of benzophenone 3,3',4,4'-tetracarboxylic acid (or 32.2 grams of benzophenone 3,3',4,4'-tetracarboxylic dianhydride) was agitated in 400 grams of distilled water to give a smooth slurry. To this was added 22.4 grams potassium hydroxide dissolved in 50 grams distilled water. While being agitated the suspension was warmed to 150° F. and held until the acid (or anhydride) had reacted to form a solution of the tetra-potassium salt. This takes 10–15 minutes. The solution was then filtered through No. 40 filter paper to remove any traces of insoluble impurities.

The preparation of the alkali metal salts of the previously described indan compound is illustrated by the example that follows:

Preparation of the Sodium Salt of Phenylindan Dicarboxylic Acid

EXAMPLE III 32.4 grams of 1,1,3-trimethyl-5-carboxy-3-(p-carboxyphenyl)indan was agitated in 300 grams distilled water to give a smooth suspension. To this was added 8.0 grams sodium hydroxide dissolved in 30 grams distilled water. While being stirred the suspension was warmed to 150° F. and held approximately 15 minutes while the acid reacted to form the di-sodium salt. The solution was filtered through No. 40 filter paper to give a clear solution ready for coating onto suitable substrates to form an R.H.-responsive film.

Other alkali metal salts including the rubidium and cesium salt can be prepared in place of the particular lithium, potassium or sodium salt illustrated in Examples I, II and III. Substantially equivalent results can be obtained with such alkali metal salts.

It was noted above that there are important industrial uses for both classes of humidity (or temperature) indicators: Those which are reversible between the birefringent and non-birefringent forms as the R.H. changes and those which are irreversible. As one can expect, a clear separation between the two classes is essential. That is, not only should the irreversible class be controllable so far as the trigger R.H. and the rate at which irreversibility occurs, but the reversible type should be free from any inadvertent irreversibility.

"Inadvertent irreversibility" is stated because the salts of some ordinarily reversible structures are of intermediate stability so that they may be used as irreversible indicators if they are appropriately nucleated (with crystals of their condensed phase, for example) just before coating and drying on an appropriate substrate. When appropriately used, these nucleated films of ordinarily reversible compounds are just as useful as those of compounds which spontaneously form irreversible birefringent polymorphs or polytypes.

Clearly there is a place for compounds of extreme resistance to the formation of irreversible polymorphs or polytypes, especially under conditions where foreign nuclei might be present which might catalyze the formation of such forms. I have found that certain complexes of the alkali metal salts of 3,3',4,4' benzophenone tetracarboxylic acid form solid, hydrated, birefringent crystals which signal humidity changes as the noncomplexed salts do but which are much more highly resistant to polymorphism or polytypism. Indeed, the most stable of these complexes form films which may be copiously seeded with the crystal nuclei of condensed phases yet no growth of the irreversible birefringent crystal phase occurs. If films of the non-complexed salts are seeded in the same fashion the entire film is converted to a birefringent irreversible form in several hours.

The first type of complex which I have discovered has unusual stability as an R.H.-responsive film. It is that which is formed between the alkali metal salts of 3,3',4,4' benzophenone tetracarboxylic acid and organic polymers containing repetitive oxygen-bearing groups including the hydroxyl, the carboxyl, the sulfonic acid group, or mixtures thereof repetitively present along a substantially linear chain. Examples of these polymers which are preferably solid and which have proven effective are as follows: methyoxy group - methoxycellulose; polyether group - polyethylene oxide; hydroxyl group - polyvinyl alcohol, hydroxyethyl cellulose; carboxyl group - poly (methyl vinyl ether/maleic anhydride), poly (styrene/maleic anhydride), poly (ethylene/maleic anhydride), polyacrylic acid; sulfonic acid group - polyvinylsulfonic acid. The carboxyl or sulfonic acid group must be neutralized with an appropriate alkali metal hydroxide so that the system as a whole is neutral or slightly basic. Further, other copolymers may be polymerized in the formation of these materials without materially altering their complexing characteristics so long as the polar groups dominate the polymer's structure. For example, polyacrylic acid may be modified by the inclusion of methacrylic acid during polymerization. Or other polymers can be copolymerized with the acrylic acid to produce highly acidic so called "acrylic emulsions" which complex as the pure polyacrylic acids do.

Polyvinylpyrrolidone is another polymer which has been found most useful in the formation of complexes with the alkali metal salts of 3,3',4,4' benzophenone tetracarboxylic acid. Though it too contains repetitive oxygen-bearing groups as do the other polymers I have found effective, unlike the others, it contains no active hydrogen. Thus, it may usefully be comixed with the others I have described to control the coating properties of the solutions of humidity-responsive salts I have described. The various polyvalent metal salts already described can be comixed with polyvinylpyrrolidone polymers (or such polymers mixed with other polymers bearing repetitive oxygen-bearing groups) which in turn are comixed with the alkali metal salts of 3,3',4,4' benzophenone tetracarboxylic acid to form materials of superior stability. The molecular weight of the polyvinylpyrrolidone is not critical, average molecular weights of 10,000, 40,000, 160,000 and 360,000 having been found suitable. Generally, however, the higher molecular weights give a higher viscosity and so the solutions compounded from such polymers coat more satisfactorily.

I have found that the molecular weight of the polymer in general is not a critical matter. Thus, a poly (styrene/maleic anhydride) resin in which there was present one mol of styrene for every mol of maleic anhydride functioned nicely as a complexing agent although the molecular weight was only 1600. On the other hand, a polyvinylsulfonic acid polymer having a molecular weight of ten million also functioned satisfactorily, as did two polyvinyl alcohols of molecular weight of 80,000 and 110,000, respectively. It is essential, of course, that the polymer or its salts, if it forms salts, be soluble in water or some appropriately volatile solvent such as an alcohol. It is also desirable that a polymer of such molecular weight be selected that the solution as compounded for coating be of an appropriate viscosity. Usually about 2% by weight of a polymer or its salt in a solution containing 15% of the alkali metal salt of 3,3',4,4' benzophenone tetracarboxylic acid forms a solution well suited for coating to form an R.H.-responsive film. 10% by weight or more of polymer can be used in order to secure good rheological properties in the coating solution.

I do not know exactly how the polymer complexing functions, but it is known that metal cations tend to bond to oxygen-containing compounds. For example, water is strongly bound to alkali metal ions in solution. Though I do not want to be limited by the concept, I theorize that the polymer network containing the oxygens of the hydroxyl, carboxyl, or sulfonic acid groups is bonded to the alkali metal ions of the unit cells of 3,3',4,4' benzophenone tetracarboxylate. For polymorphs to form, wholly new crystal structures must be formed. I theorize that the polymer network with its myriad bonding points greatly restricts the movement of metal ions and so substantially reduces the possibility of polymorphic changes.

I have discovered still another mode of complexing and this too reduces the possibility of polymorphic change due to accidental nucleation. Or, if films of reversible crystal structures are seeded with condensed phase crystals, the polymorphic transition is greatly slowed. This second method of complexing comprises adding water soluble salts of the following metals to the alkali metal 3,3',4,4' benzophenone tetracarboxylate coating solution: $Cu^{++}$, $Ni^{++}$, $Co^{++}$, $Mn^{++}$, $Al^{+++}$, $Be^{++}$, $Zn^{++}$, $Ca^{++}$, $Cd^{++}$, $Sr^{++}$, $Ba^{++}$, $Mg^{++}$, and $Cr^{+++}$. Typical anions which usually confer water solubility on these cations are the sulfate, nitrate, acetate, chloride, or even in some instances the 3,3',4,4' benzophenone tetracarboxylate ion. In some instances it is helpful to add more than one metal ion in order to secure synergistic action.

I have found that usually about 6 mol percent of the metals present in the alkali metal 3,3',4,4' benzophenone tetracarboxylate/polyvalent metal salt mixture must be a suitable polyvalent metal to control polymorphic changes. However, as little as 0.5 mol percent of the polyvalent metal can be helpful and as much as 25 mol percent may be necessary for superb stability.

As before, I am not sure of the exact mechanism through which these polyvalent ions work. But I theorize that the inclusion of polyvalent ions forms bridge complexes among the tetravalent 3,3',4,4' benzophenone carboxylate ions. These myriad bridges throughout the system form a network and contribute rigidity and so minimize the movement of molecules which is essential for polymorphic changes.

My third group of complexes comprises (a) the polar polymers mentioned before which contain hydroxyl, carboxyl, or sulfonic acid groups, (b) the water-soluble salts of the polyvalent metal ions noted above, and (c) the alkali metal salts of 3,3',4,4' benzophenone tetracarboxylic acid. Such a complex confers remarkable resistance to polymorphism. For example, films of such complexes are very responsive to R.H. changes yet even when seeded with condensed phase crystals no polymorphic change occurs. Without the polar polymer and the salt of the polyvalent metal present condensed phase crystals bring about total polymorphic conversion in a few hours.

The use of both polar polymer and polyvalent salt is far more effective than either complexing material used alone, though the concentrations of the reactants found suitable are still the same. As an indication of the strength of the bonding which occurs, an alkali metal 3,3',4,4' benzophenone tetracarboxylate complexed with polyvinyl alcohol and a magnesium/copper salt mixture was titrated with potassium hydroxide solution to a pH of 10.0 to form a sparkling clear solution permanently free of any metal hydroxide. Titration of the same metal salts merely dissolved in water immediately formed an opaque sludge of metal hydroxides before pH 9.0 was reached. The other polar polymers tabulated above gave solutions in which the metals were complexed in the same highly stable way.

An example of a solution system which on coating onto a suitable substrate deposits a solid film which at approximately 52 R.H. forms birefringent, hydrated crystals follows, the formula being given in parts by weight:

200 parts tetrapotassium 3,3',4,4' benzophenone tetracarboxylate solution, 25% 25 parts magnesium sulfate solution, 7% 2 parts cupric acetate solution, 5% 96 parts polyvinyl alcohol solution, 8% (molecular weight 110,000)
66 parts water 389 parts Total Summarizing, the exact bonding in these complexes is unknown. But the remarkable change in the lability of the constituent alkali metal 3,3',4,4' benzophenone tetracarboxylate molecule—as indicated by its freedom from polymorphism or polytypism—while preserving the R.H.-response of the complex suggest strong binding forces are involved. For the attractive forces which bring about polymorphic changes are quite powerful. Still another confirmation of the strength of the complexing is the substantial rise in the relative humidity at which any particular alkali metal 3,3',4,4' benzophenone tetracarboxylate composition passes from isotropic to the birefringent, hydrated, crystalline mode. In general, the complexed material has an R.H. "trigger point" almost 10% R.H. higher than that possessed by the same pure alkali metal salt.

In U.S. Pat. No. 3,776,038 it is noted that the alkali salts of 1,1,3-trimethyl-5-carboxy-3-(p-carboxyphenyl) indan are useful as compounds which in themselves sense changes in relative humidity. In particular, as they attain the anisotropic state, certain organizational forces operating within a period of from a few hours to several days cause irreversible birefringent crystals to form. These permanently record the fact that for at least that period the relative humidity (RH) had exceeded the "trigger point" of the particular film. The trigger point may be chosen by using blends of the various alkali salts (Li, Na, K, Rb, and Cs) of the indan compound.

For many applications a more rapid shift to the irreversible form of crystal is desirable. That is, a shift to the "recording" form in a few minutes instead of a few hours or a few days is highly useful since it gives a more sensitive indication of when materials packaged with silica gel are nearing the end of the period during which moisture levels are successfully controlled.

I have now discovered novel chemical structures which respond very quickly to any humidity level beyond their stability level. That is, once the "trigger point" is passed, an opaque crystal structure very rapidly develops and this may be observed by the eye alone, by the eye with Polaroids to amplify the effect, or with suitable electronic photo-responsive devices such as photoelectric cells.

The first series of sensitive compounds are those based on the alkali salts of pamoic acid (4,4'-methylene bis (3-hydroxy-2-naphthoic acid). By mixing varying ratios of the various pamoate salts (disodium pamoate, dipotassium pamoate, etc.), compounds may be prepared which pass from one level of hydration to another at a definite relative humidity (RH). At the "trigger point" a pronounced optical effect is noted, a clear film of the compound turning to an opaque white film.

Since this moisture-sensitive film is prepared from a water solution of the alkali pamoates, it might be expected that the opaque white film would form during preparation of the film. But I have found that if a thin film of the pamoate solution is rapidly dried, the water flashes away leaving a clear glass-like film. Apparently there is too little time for the molecular rotation effects, which it is thought lead to the formation of the white, irreversible crystal, to take effect. A suitable drying rate to form the glassy film has been secured using drying temperatures in the 250°–350° F. range.

The clear, glassy films may be stored below the triggering humidity for many months without opacity developing. It is only when the trigger point is passed that opacity develops.

It was found that the alkali pamoates could be mixed with the alkali salts of 3,4,3',4' benzophenone tetracarboxylic acid in various ratios to prepare blends which also triggered to opaque, irreversible films.

The second series of compounds which rapidly convert from clear films to opaque white irreversible films when their trigger points have been passed are the alkali salts of o benzoyl benzoic acid and halobenzoyl benzoic acid. Varying ratios of the alkali salts of these acids may be mixed to give materials which trigger at different relative humidities. Further, the salts of these two acids may be mixed or these salts can be co-mixed with the alkali metal salts of 3,4,3',4' benzophenone tetracarboxylic acid to give compounds useful in signalling RH levels irreversibly. As before, films of these solutions are prepared by rapidly drying a film on a suitable substrate.

The third series of compounds which rapidly convert from clear films to irreversible opaque films when their trigger RH has been passed are the mono-acid, tri-alkali salts of 3,4,3',4' benzophenone tetracarboxylic acid (BTCA). U.S. Pat. No. 3,776,038 describes the normal tetra-alkali salts of this compound as useful for the reversible sensing of humidity levels to which the compounds or films of the compounds are exposed. I have now found that the acid salts of these various alkali metals are useful for the preparation of films which remain clear below a critical RH but which trigger to a white, opaque form above the critical RH.

Though a salt may be prepared which is somewhat more acid than $X_3H$ BTCA (where X is an alkali metal such as Li, Na, K, Rb, and Cs), the monohydrogen salt is soluble, readily coated onto substrates, and rapidly converts to an opaque form under conditions of appropriate humidity.

U.S. Pat. No. 3,776,038 covers the use of the alkali salts of 3,4,3',4' benzophenone tetracarboxylic acid (BTCA) as compounds which in themselves sense changes in relative humidity (RH) to which they are exposed. The compound's optical properties vary as the humidity changes, the compounds passing clear, isotropic forms at one RH to translucent, anisotropic forms at another RH. For ease of indication the compounds may be printed in the form of numbers, or they may be coated as film in the form of circles, squares, or other shapes. As the patent makes clear, the coatings may exist as solutions on the substrate as well as in the solid form. So long as the substrate on which the compounds are coated is substantially horizontal, no "drainage" problems are encountered. However, during the solution phase gravity may cause the solution to run or drip if the substrate is in a vertical position.

U.S. Pat. No. 3,776,038 notes that these drainage problems may be minimized in several ways, including the application of the responsive compounds in the form of droplets. However, field experience has shown that it is very difficult to prevent drainage problems when the ambient humidity is very high and the total volume of liquid in each droplet or plaque is quite high due to sorption of moisture from the air. For though surface tension effects may control drainage when the films or droplets are first applied to clean substrates during manufacture, exposure in the field allows monomolecular films having varying surface tension properties to build up through sorption effects. It is thought that these monolayers contribute to the dripping and drainage problems sometimes encountered with this type of humidity-responsive film when used in the vertical mode.

I have now found that these drainage problems can be controlled through the additional coating of the substrate with very finely divided particles so as to create a micro-roughness above the substrate surface. The solutions of the alkali salts of BTCA are illustrative of salt solutions whose dripping or draining can be controlled. Elsewhere, I have described other salt solutions whose films or droplets are useful in sensing humidity changes. Included among these solutions were the reaction products of certain polyvalent metal salts (such as magnesium sulfate, $Mg_2$ BTCA, and chromium sulfate) and the alkali salts of BTCA. I include these materials among the salt solutions whose drainage on substrates may be controlled in the manner described. Also, I include the specific compounds tested in the claims of U.S. Pat. No. 3,776,038. Specifically, I claim controlling the drainage problems in humidity-responsive instruments which utilize the chemical compounds described above.

Among the very finely divided materials which may be used to confer the necessary micro-roughness to the substrate are the so-called fumed silicas, very small silicon dioxide particles manufactured by burning silicon tetrachloride. The size of such particles generally ranges from about 0.06 to 0.004 microns. Of special value for use in controlling drainage are such silicon dioxide particles which have been treated with silane so as to form trimethylsilyl groups on the surface of the silicon dioxide. Water, on surfaces appropriately treated with silane modified silicon dioxide exhibits contact angles of from 125° to 150° and it is such a material that is particularly useful in treating the substrates. Other finely divided silicas and silicates may be treated with silane or silane homologs to secure somewhat similar results and such materials also may be used.

The finely divided particles may be applied mechanically to the substrate which is coated with the dried salts. Under such circumstances electrostatic forces usually hold tenaciously a thin, dense coat of particles. However, the finely divided particles may be dispersed in a carrier liquid which exhibits no substantial solvency toward the salts used. Xylene or toluene exemplify solvents of general utility for this purpose. The substrate may then be dipped in such a slurry and dried, or the slurry may be sprayed onto the salt coated substrate. For exceptionally good adherence and ruggedness under rough handling, a bonding adhesive may be incorporated in the silicon dioxide or silane-treated silicon dioxide slurry. A silicone-type of adhesive such as Dow Corning's 282 Adhesive is especially useful for such purposes. A suitable coating suspension has been found to comprise 2% silane-coated silicon dioxide, 1% DC 282 Adhesive, and 97% toluene. Using such a substrate coating, salt droplets showed no tendency to run or drain on a vertical substrate under 100% RH conditions.

I have also found that the drainage problems described above may be effectively controlled by coating the films or droplets of the humidity-indicating salt and the substrate on which they are deposited with at least a mono-molecular coating of an appropriate silane or silicone. Dipping, spraying, or vaporphase treatment may be used to deposit the coating. Chlorosilanes such as methyltrichlorosilane, dimethyldichlorosilane, or trimethylchlorosilane may be used. Methylsilazanes such as hexamethyldisilazine, or alkoxysilanes such as methyltrimethoxysilane may also be used, the latter being especially useful since only inert alcohol is generated as a byproduct. Silicones of high water-repellency may also be used.

I have disclosed in my application Ser. No. 18,921, filed Mar. 12, 1970 that the alkali salts of 1,1,3-trimethylcarboxy-3-(p-carboxyphenyl) indan are useful irreversible visual-type humidity-responsive indicators. Though their slowness in triggering is mentioned, there is a still greater problem: the organic acid from which these salts are made is of such an unusual structure as to necessitate very high prices for the acid, thus precluding the use of its salts for many indicating purposes. Thus, there exists a very real need for suitable irreversible visual indicators of ambient humidity levels based on more readily available, less expensive acids and salts. Further, there is a need for visual indicators which change their optical properties so drastically, once the "triggering" humidity level is reached, that Polaroid amplifiers are not needed. For the use of Polaroids adds substantially to the cost of such indicator systems.

I have claimed in my recent application, Ser. No. 505,526, filed Sept. 12, 1974, which is a continuation-in-part of application Ser. No. 245,494, filed Apr. 19, 1972, the use of the solid, crystalline, hydrated, birefringent alkali metal salts of (a) benzoyl benzoic acid, (b) substituted benzoyl benzoic acid, (c) halogenated benzoyl benzoic acids, and (d) 4,4'-methylene bis (3-hydroxy-2-naphthoic acid) as visual-type humidity-responsive indicators. These are all readily available, relatively inexpensive acids. I also have claimed the use of these compounds comixed with the alkali metal salts of 3,3',4,4' benzophenone tetracarboxylic acid. I have now found that these same compounds, as well as comixtures with the various alkali metal salts of 3,3',4,4' benzophenone tetracarboxylate acid, can be much more effective signalling agents, even when polarizers are not used for visual amplification, through the comixing of these various salts with certain crystal structure modifiers. The signalling salts ordinarily turn from clear to opalescent when the trigger point is reached. With the irreversible type of compound, a conversion to the irreversible crystal form then begins. With some compounds the conversion may be quite slow and the opalescent layer may not become substantially more opaque during the conversion. Other materials may convert rapidly to rather opaque films. But I have found that virtually all compounds not containing crystal structure modifiers tend to form films or layers of less than the opacity of which they are capable if the ambient humidity rises above the trigger humidity of the particular compound very, very slowly.

The phenomenon, of course, occurs because of the well known fact that large crystals form when the differential factor which is causing crystal growth (change in solubility, change in humidity, etc.) is very small. Small crystals, in turn, normally form when the differential causing growth is very large. Characteristically, in a sealed package containing silica gel to maintain a low safe storage humidity for an encapsulated article, into which moisture is leaking at a very slow rate through pinholes, etc., the ambient humidity within the package rises very, very slowly. It is under such typical industrial storage conditions that these humidity-responsive indicating compounds tend to convert to films which are of substantially lower opacity than would be secured if the ambient humidity rose rapidly above the trigger point. Through the use of crystal structure modifiers, however, indicating compounds may be formulated which form high opacity films even when the ambient humidity rises very, very slowly.

These crystal structure modifiers have the common attribute of substantially lowering the surface tension of the solutions of humidity-responsive salts though their structures may vary widely. For example, such compounds as the following have proven active: the alkali metal dialkyl sulfosuccinates, the alkali metal lauryl sulfates, the alkyphenoxy polyethoxy ethanols, polyoxyethylene derivatives of sorbitan fatty acid esters, polyoxyalkylene fatty acid esters, polyoxyalkylene fatty ethers, the alkali metal alkylaryl polyether sulfonates, and the alkali metal alkylaryl ether sulfates. Such materials are distinguished by their ability to reduce the surface tension of distilled water into the 30–40 dynes/cm. range when 100 ppm. of the agent is added to the water. The same order of effectiveness in surface tension reduction is encountered when these agents are used with solutions of humidity-responsive salts.

There is a special group of surface active modifiers distinguished by both their ability to lower surface tension to unusually low levels and their concurrent ability to bring about unusually rapid conversion from the reversible crystal form to an irreversiable crystal form of unusually high opacity. These agents are of such effectiveness that 100 ppm. will reduce the surface tension of distilled water to approximately 15–25 dynes/cm.

The agents which possess these remarkable properties are materials whose chemical structure is characterized by a stable fluorocarbon tail, $F_3C(CF_2CF_2 \ldots )$ attached to a solubilizing group X which can be anionic, cationic, or nonionic. I am not certain of the mechanism of the action of these compounds. Perhaps the very low degree of interaction between fluorocarbon chains allows unusual mobility of these molecules within the crystal structure of the solid humidity-responsive salt. If such is the case, sorption complexes may form during polymorphic or polytypic transitions so that certain preferred crystal structures tend to form. In any case, as one type of solid crystal changes to another type of solid crystal, crystal structures of unusual opacity develop even under very difficult conditions.

In my U.S. Pat. No. 3,776,038, column 6, line 24, I mention the use of ordinary wetting agents to lower the surface tension of humidity-responsive salt solutions so that they may adequately wet the substrate on which they are being deposited. By happenstance these new fluorinated crystal structure modifiers just described have the concurrent property of lowering the surface tension of solutions in which they are dissolved. But the critical function of these crystal structure modifiers and what is claimed here is their use in the solid, crystalline state—not in solution. It is in the solid state, perhaps as complexes of some type with the humidity-responsive salts, that they perform their remarkable function of directing the polymorphic or polytypic change of the solid salts to new structures of high opacity and unusual commercial utility. And they so function even when the humidity is changing very slowly and thus the phase change is progressing very slowly in the crystalline coating.

These crystal structure modifiers are of general utility in usefully directing polymorphic and/or polytypic phase transitions in the alkali metal salts or their comixtures which of themselves sense changes in humitity and which are abruptly triggered at a predetermined relative humidity level from an isotropic state at a first relative humidity to an anisotropic state at a second relative humidity. But they are particularly effective when used with those humidity-responsive salts which in their state of substantial hydration are markedly prone to polymorphic or polytypic transitions. The alkali metal salts of their comixtures of benzoyl benzoic acid, of substituted benzoyl benzoic acids, or of 4,4' methylene bis (3-hydroxy-2-naphthoic/acid) typify such compounds. If such polymorphic transitions occur too rapidly in the presence of these crystal structure modifiers, the rate of change may be slowed down by comixing appropriate alkali metal salts of 3,3',4,4' benzophenone tetracarboxylic acid with the compounds. For the highly symmetrical structure of the alkali salts or their comixtures of this latter acid tends to slow down the polymorphic changes in alkali salts or their comixtures of less symmetrical structures.

Though ordinarily 0.005 to 0.10% by weight of these various crystal-structure modifying agents is added to the 25% solids by weight salt solution before drying to form the comixed solid, 0.40% or even more may be used to secure a very high degree of opacity of the hydrated, birefringent, crystalline solid.

What is claimed is:

1. The solid, crystalline, hydrated, birefringent tetraalkali salts of 3,3',4,4' benzophenone tetracarboxylic acid consisting of the group of Li, K, Rb, and Cs.

2. A mixed crystal of the tetraalkali metal salts of 3,3',4,4' benzophenone tetracarboxylic acid in which at least two different alkali metals are present and function as equivalents to form solid, hydrated, crystals of the non-cubic system.

3. A mixed crystal of the tetra (lithium, sodium) salts of 3,3',4,4' benzophenone tetracarboxylic acid in which lithium and sodium function as equivalents to form solid, hydrated, crystals of the non-cubic system.

4. A mixed crystal of the tetra (sodium, potassium) salts of 3,3',4,4' benzophenone tetracarboxylic acid in which sodium and potassium function as equivalents to form solid, hydrated, crystals of the non-cubic system.

5. A mixed crystal of the tetra (potassium, rubidium) salts of 3,3',4,4' benzophenone tetracarboxylic acid in which potassium and rubidium function as equivalents to form solid, hydrated, crystals of the non-cubic system.

6. The solid, crystalline, hydrated, birefringent alkali metal salts of 3,3',4,4' benzophenone tetracarboxylic acid in which one hydrogen is left unneutralized.

7. A mixed crystal of the solid, crystalline, hydrated, birefringent alkali metal salts of 3,3',4,4' benzophenone tetracarboxylic acid in which one hydrogen is left unneutralized and at least two different alkali metals are present and function as equivalents.

* * * * *